US00PP16181P2

(12) United States Plant Patent
Gossett

(10) Patent No.: US PP16,181 P2
(45) Date of Patent: Jan. 3, 2006

(54) ×*HEUCHERELLA* PLANT NAMED 'PARTY TIME'

(50) Latin Name: ×*Heucherella* sp.
Varietal Denomination: Party Time

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 150 days.

(21) Appl. No.: 10/871,738

(22) Filed: Jun. 18, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP11,081 P * 10/1999 Oliver ..... Plt./263
PP12,164 P2 * 10/2001 Heims ..... Plt./263

OTHER PUBLICATIONS http://www.terranovanurseries.com/pages/plantsH6.html.*
http://www.plantdelights.com/Catalog/Current/page33.html.*

* cited by examiner

*Primary Examiner*—Kent Bell
*Assistant Examiner*—W. C. Haas
(74) *Attorney, Agent, or Firm*—Klarquist Sparkman, LLP

(57) ABSTRACT

A new and distinct cultivar of ×*Heucherella* plant characterized by its abundant warm pink flowers, compact habit, and maple shaped leaves.

1 Drawing Sheet

Botanical designation: ×*Heucherella* sp.
Variety denomniation: 'Party Time'.

BACKGROUND OF THE INVENTION

The present invention relates to a new and distinct intergeneric hybrid between *Heuchera* and *Tiarella*, given the cultivar name 'Party Time'. Both genera, *Heuchera* and *Tiarella*, are of the family Saxifragaceae. This intergeneric hybrid is know as ×*Heucherella*.

This new cultivar originated as a single plant from crossing a group of selected *Heuchera* hybrids with massed pollen from a group of selected *Tiarella* hybrids. The specific parent plants are unknown.

SUMMARY OF THE INVENTION

This new ×*Heucherella* is distinguished by:

1. Prolific bloom.
2. Warm pink flower color.
3. Compact habit.
4. Maple shaped leaves with a slight white veil, and darkening along the main veins.
5. Excellent vigor.

The new variety has been reproduced only by asexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing charateristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old plant of the new variety growing in the spring in the ground in trial fields in Canby, Oreg.

DETAILED PLANT DESCRIPTION

The following is a detailed description of the new ×*Heucherella* hybrid based on observations of two-year-old specimens grown in the ground in full sun under typical outdoor conditions the trial fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical name: ×*Heucherella*.
Cultivar name: 'Party Time'.
Plant:
- *Type.*—Herbaceous perennial.
- *Form.*—Basal rosette.
- *Hardiness.*—USDA Zone 5.
- *Size.*—18 cm tall from the ground to the top of the foliage and 35 cm wide.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate.

*Lobing/division.*—5 lobes (plus two small lobes at the bottom on some leaves ). Lobes are cut ½ way to the midrib, broadly oblong, with the terminal lobe having two secondary lobes.

*Venation.*—Palmate.

*Margins.*—Crenate.

*Apex.*—Mucronulate.

*Base.*—Cordate.

*Blade size.*—Ranges from 5 to 9 cm long and 5.5 to 8 cm wide.

*Surface texture.*—Sparsely pubescent.

*Petiole size.*—Ranges from 10 to 14.5 cm long and 2 mm wide.

*Petiole surface.*—Pubescent and with glandular hairs.

*Petiole color.*—Yellow Green 146C near blade and Greyed Orange 165A near base.

*Leaf color.*—Spring leaves — Abaxial side — Green 138A on and along veins and margins, with a light veil over the rest giving it the Yellow Green 146B cast, and a dark pattern along the main veins toward the leaf base, Greyed Purple 183A. Adaxial side — Yellow Green 147B. Winter leaves — Red Brown, Brown 200B with a silvery veil, Grey 201C. Veins Green 138A.

Inflorescence:

*Type.*—Thyrse.

*Number of thyrse in first spring flush.*—75.

*Number of flowers.*—Ranges from 65 to 150 per thyrse, on top 17 cm to 20 cm of peduncle.

*Peduncle.*—With 1 to 5 leaves and flowering branches. Height — 40 cm. Diameter — 0.2 cm. Color — Burgundy, Greyed Purple 183A. Surface — Glandular hairs.

*Pedicel.*—Length — 0.5 cm to 2 cm. Surface — Glandular hairs. Color — Greyed Purple 183A.

*Bloom period.*—Early April to late May. Sporadic rebloom until fall in Canby. Oreg.

Flower bud:

*Size.*—0.4 cm deep and 0.2 cm wide.

*Description.*—Oblong, downfacing, with glandular hairs.

*Color.*—Deep pink, Greyed Purple 185C.

*Flower:*

*Type.*—Perfect, sepals petaloid.

*Shape.*—Campanulate.

*Size.*—0.9 cm wide and 0.6 cm deep.

*Petal count.*—5.

*Petal shape.*—Oblanceolate with a clawed base, apex acute, margin entire.

*Petal size.*—0.5 cm long and 0.1 cm wide.

*Petal color.*—Pink, Red Purple 63C on inner and outer surface.

*Petal surface texture.*—Satiny.

*Calyx.*—Petaloid, divided ⅔ the way to the base, with glandular hairs.

*Calyx shape.*—Campanulate with 5 rounded entire lobes, apex acute.

*Calyx size.*—0.6 cm wide and 0.4 cm deep.

*Calyx surface texture.*—Glandular pubescent.

*Calyx color.*—Outside: Red purple 63D at base darkening toward Red Purple 63B at lobe, with an even darker spot of Greyed Purple 185A at apex. Inside: Same as above.

*Stamen.*—5, sterile filaments of White 55D are 3 mm long terminated with oval, flattened anthers, 0.1 mm wide and 0.15 mm deep, no pollen produced.

*Pistil.*—1, 7 mm long, White 55D overall, ovoid and two-lobed, each lobe is 2.5 mm long terminated in a narrow stigma.

*Fragrance.*—None.

*Lastingness.*—A thyrse blooms for about 2 weeks on the plant.

Fruit:

*Type.*—Occasional *Heuchera* like two-parted capsules are formed.

*Size.*—4 mm to 7 mm.

*Color.*—Yellow Green 150C prior to shriveling and aborting.

Seed: None observed.

Fertility: Usually sterile.

Pest and disease tolerance: No major pest or disease problems. All ×*Heucherella* may be damaged by root weevils.

COMPARISONS TO SIMILAR ×*HEURECHERELLA*

Compared to ×*Heucherella* 'Dayglow Pink' (U.S. Plant Pat. No. 12,164), this new cultivar has more flowers per peduncle and over a wider area of the peduncle and a different leaf shape, broader and more simply lobed. ×*Heucherella* 'Party Time' also has a slightly veiled leaf unlike 'Dayglow Pink'.

I claim:

1. A new and distinct cultivar of ×*Heucherella* plant as herein illustrated and described.

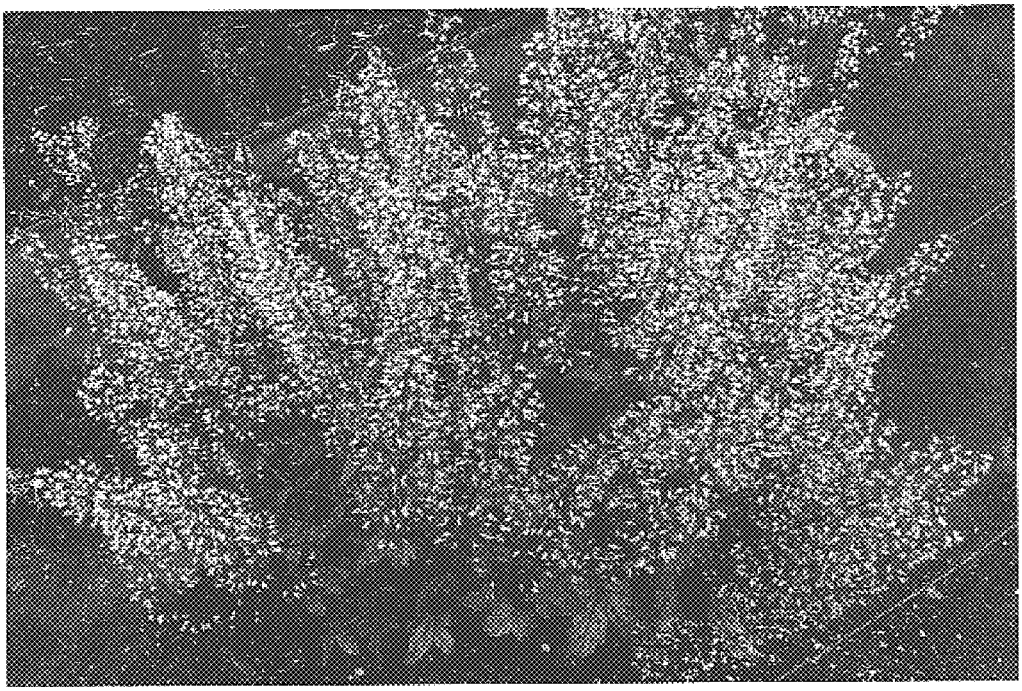

* * * * *